US012364276B2

(12) United States Patent
Li et al.

(10) Patent No.: US 12,364,276 B2
(45) Date of Patent: Jul. 22, 2025

(54) **PROBIOTIC FOR INHIBITING GROWTH OF *PROTEUS MIRABILIS*, AND FERMENTATION BROTH AND APPLICATION THEREOF**

(71) Applicant: ALAND BIOTECHNOLOGY RESEARCH TAIZHOU CO., LTD, Taizhou (CN)

(72) Inventors: Xuejun Li, Taizhou (CN); Gordon Zhang, Taizhou (CN); Yu Zhao, Taizhou (CN); Chengwei Xu, Taizhou (CN)

(73) Assignee: IVC NUTRITION CORPORATION, Taizhou (CN)

( * ) Notice: Subject to any disclaimer, the term of this patent is extended or adjusted under 35 U.S.C. 154(b) by 571 days.

(21) Appl. No.: 17/689,927

(22) Filed: Mar. 8, 2022

(65) Prior Publication Data

US 2022/0192247 A1    Jun. 23, 2022

Related U.S. Application Data

(63) Continuation of application No. PCT/CN2021/102388, filed on Jun. 25, 2021.

(30) Foreign Application Priority Data

May 14, 2021   (CN) .......................... 202110530026.7

(51) Int. Cl.
| | | |
|---|---|---|
| *A23L 33/135* | (2016.01) | |
| *A61K 35/745* | (2015.01) | |
| *A61K 35/747* | (2015.01) | |
| *A61P 9/10* | (2006.01) | |
| *A61P 31/04* | (2006.01) | |

(52) U.S. Cl.
CPC .......... *A23L 33/135* (2016.08); *A61K 35/745* (2013.01); *A61K 35/747* (2013.01); *A61P 9/10* (2018.01); *A61P 31/04* (2018.01); *A23V 2400/113* (2023.08); *A23V 2400/125* (2023.08); *A23V 2400/143* (2023.08); *A23V 2400/165* (2023.08); *A23V 2400/169* (2023.08); *A23V 2400/173* (2023.08); *A23V 2400/175* (2023.08); *A23V 2400/515* (2023.08); *A23V 2400/517* (2023.08); *A23V 2400/529* (2023.08)

(58) Field of Classification Search
CPC .......... A23L 33/135; A61P 9/10; A61P 31/04
See application file for complete search history.

(56) References Cited

U.S. PATENT DOCUMENTS 10,058,576 B2 *   8/2018   Bushman .................. C12N 1/20

FOREIGN PATENT DOCUMENTS

| CN | 105189732 A | * 12/2015 | ........... A61K 35/741 |
|---|---|---|---|
| CN | 109223832 A |   1/2019 | |
| CN | 110257306 A |   9/2019 | |
| CN | 110621332 A |  12/2019 | |
| JP | 2017201983 A |  11/2017 | |

* cited by examiner

*Primary Examiner* — Mary Maille Lyons

(57) ABSTRACT

A probiotic for inhibiting growth of *Proteus mirabilis*, including a microorganism selected from the group consisting of *Lactobacillus rhamnosus*, *Lactobacillus fermentum*, *Lactobacillus plantarum*, *Lactobacillus casei*, *Lactobacillus acidophilus*, *Lactobacillus paracasei*, *Lactobacillus reuteri*, *Bifidobacterium animalis* subsp. *lactis*, *Bifidobacterium infantis*, *Bifidobacterium bifidum* and a combination thereof. A fermentation broth and an application of the probiotic are further provided.

4 Claims, 6 Drawing Sheets

Specification includes a Sequence Listing.

SEQUENCE LISTING

```
<160> NUMBER OF SEQ ID NOS: 10

<210> SEQ ID NO 1
<211> LENGTH: 1452
<212> TYPE: DNA
<213> ORGANISM: Artificial Sequence
<220> FEATURE:
<223> OTHER INFORMATION: synthetic

<400> SEQUENCE: 1
gtatacatgc aagtcgaacg agttctgatt attgaaaggt gcttgcatct tgatttaatt      60
ttgaacgagt ggcggacggg tgagtaacac gtgggtaacc tgcccttaag tggggataa     120 catttggaaa cagatgctaa taccgcataa atccaagaac cgcatggttc ttggctgaaa     180
gatggcgtaa gctatcgctt ttggatggac ccgcggcgta ttagctagtt ggtgaggtaa     240
cggctcacca aggcaatgat acgtagccga actgagaggt tgatcggcca catttgggact     300 gagacacggc ccaaactcct acgggaggca gcagtaggga atcttccaca atggacgcaa     360
```

```
gtctgatgga gcaacgccgc gtgagtgaag aaggctttcg ggtcgtaaaa ctctgttgtt      420
ggagaagaat ggtcggcaga gtaactgttg tcggcgtgac ggtatccaac cagaaagcca      480
cggctaacta cgtgccagca gccgcggtaa tacgtaggtg gcaagcgtta tccggattta      540
ttgggcgtaa agcgagcgca ggcggttttt taagtctgat gtgaaagccc tcggcttaac      600
cgaggaagtg catcggaaac tgggaaactt gagtgcagaa gaggacagtg gaactccatg      660
tgtagcggtg aaatgcgtag atatatggaa gaacaccagt ggcgaaggcg gctgtctggt      720
ctgtaactga cgctgaggct cgaaagcatg ggtagcgaac aggattagat accctggtag      780
tccatgccgt aaacgatgaa tgctaggtgt tgagggtttt ccgccccttca gtgccgcagc      840 taacgcatta agcattccgc ctggggagta cgaccgcaag gttgaaactc aaaggaattg      900
acggggcccc gcacaagcgg tggagcatgt ggtttaattc gaagcaacgc gaagaacctt      960
accaggtctt gacatctttt gatcacctga gagatcaggt ttccccttcg ggggcaaaat     1020
gacaggtggt gcatggttgt cgtcagctcg tgtcgtgaga tgttgggtta agtcccgcaa     1080
cgagcgcaac ccttatgact agttgccagc atttagttgg gcactctagt aagactgccg     1140
gtgacaaacc ggaggaaggt ggggatgacg tcaaatcatc atgccccctta tgacctgggc     1200 tacacacgtg ctacaatgga tggtacaacg agttgcgaga ccgcgaggtc aagctaatct     1260
cttaaagcca ttctcagttc ggactgtagg ctgcaactcg cctacacgaa gtcggaatcg     1320
ctagtaatcg cggatcagca cgccgcggtg aatacgttcc cgggccttgt acacaccgcc     1380
cgtcacacca tgagagtttg taacacccga agccggtggc gtaaccctttt agggagcga     1440 gccgtctaag gg                                                         1452

<210> SEQ ID NO 2
<211> LENGTH: 1459
<212> TYPE: DNA
<213> ORGANISM: Artificial Sequence
<220> FEATURE:
<223> OTHER INFORMATION: synthetic

<400> SEQUENCE: 2
tgctatacat gcaagtcgaa cgcgttggcc caattgattg atggtgcttg cacctgattg       60
attttggtcg ccaacgagtg gcggacgggt gagtaacacg taggtaacct gcccagaagc      120 ggggggacaac atttggaaac agatgctaat accgcataac aacgttgttc gcatgaacaa      180
cgcttaaaag atggcttctc gctatcactt ctggatggac ctgcggtgca ttagcttgtt      240
ggtggggtaa cggcctacca aggcgatgat gcatagccga gttgagagac tgatcggcca      300
caatgggact gagacacggc ccatactcct acgggaggca gcagtaggga atcttccaca      360
atgggcgcaa gcctgatgga gcaacaccgc gtgagtgaag aagggtttcg gctcgtaaag      420
ctctgttgtt aaagaagaac acgtatgaga gtaactgttc atacgttgac ggtatttaac      480
cagaaagtca cggctaacta cgtgccagca gccgcggtaa tacgtaggtg gcaagcgtta      540
tccggattta ttgggcgtaa agagagtgca ggcggttttc taagtctgat gtgaaagcct      600
tcggcttaac cggagaagtg catcggaaac tgggataactt gagtgcagaa gagggtagtg      660
gaactccatg tgtagcggtg gaatgcgtag atatatggaa gaacaccagt ggcgaaggcg      720
gctacctggt ctgcaactga cgctgagact cgaaagcatg ggtagcgaac aggattagat      780
accctggtag tccatgccgt aaacgatgag tgctaggtgt tgagggttt ccgcccttca      840 gtgccggagc taacgcatta agcactccgc ctggggagta cgaccgcaag gttgaaactc      900
```

```
aaaggaattg acggggcccc gcacaagcgg tggagcatgt ggtttaattc gaagctacgc    960
gaagaacctt accaggtctt gacatcttgc gccaaccccta gagatagggc gtttccttcg  1020
ggaacgcaat gacaggtggt gcatggtcgt cgtcagctcg tgtcgtgaga tgttgggtta  1080
agtcccgcaa cgagcgcaac ccttgttact agttgccagc attaagttgg cactctagt   1140
gagactgccg gtgacaaacc ggaggaaggt ggggacgacg tcagatcatc atgccccta   1200
tgacctgggc tacacacgtg ctacaatgga cggtacaacg agtcgcgaac tcgcgagggc  1260
aagcaaatct cttaaaaccg ttctcagttc ggactgcagg ctgcaactcg cctgcacgaa  1320
gtcggaatcg ctagtaatcg cggatcagca tgccgcggtg aatacgttcc cgggccttgt  1380
acacaccgcc cgtcacacca tgagagtttg taacacccaa agtcggtggg gtaacctttt  1440
aggagccagc cgcctaagt                                                1459
```

```
<210> SEQ ID NO 3
<211> LENGTH: 1460
<212> TYPE: DNA
<213> ORGANISM: Artificial Sequence
<220> FEATURE:
<223> OTHER INFORMATION: synthetic

<400> SEQUENCE: 3
```

```
cgggtctata catgcagtcg agcgagctga accaacagat tcacttcggt gatgacgttg     60
ggaacgcgag cggcgatgg gtgagtaaca cgtggggaac ctgccccata gtctgggata   120
ccacttggaa acaggtgcta ataccggata agaaagcaga tcgcatgatc agcttataaa   180
aggcggcgta agctgtcgct atgggatggc ccgcgcgtgc attagctagt ggtagggta   240
acggcctacc aaggcaatga tgcatagccg agttgagaga ctgatcggcc acattgggac   300
tgagacacgc cccaaactcc tacgggaggc agcagtaggg aatcttccac aatggacgaa   360
agtctgatgg agcaacgccg cgtgagtgaa gaaggttttc ggatcgtaaa gctctgttgt   420
tggtgaagaa ggatagaggt agtaactggc ctttatttga cggtaatcaa ccagaaagtc   480
acggctaact acgtgccagc agccgcggta atacgtaggt ggcaagcgtt gtccggattt   540
attgggcgta aagcgagcgc aggcggaaga ataagtctga tgtgaaagcc ctcggcttaa   600
ccgaggaact gcatcggaaa ctgttttct tgagtgcaga agaggagagt ggaactccat   660
gtgtagcggt ggaatgcgta gatatatgga agaacaccag tggcgaaggc ggctctctgg   720
tctgcaactg acgctgaggc tcgaaagcat gggtagcgaa caggattaga taccctggta   780
gtccatgccg taaacgatga gtgctaagtg ttgggaggtt tccgcctctc agtgctgcag   840
ctaacgcatt aagcactccg cctggggagt acgaccgcaa ggttgaaact caaaggaatt   900
gacggggccc cgcacaagcg gtggagcatg tggtttaatt cgaagcaacg cgaagaacct   960
taccaggtct tgacatctag tgcaatccgt agagatacgg agttcccttc ggggacacta  1020
agacaggtgg tgcatggctg tcgtcagctc gtgtcgtgag atgttgggtt aagtcccgca  1080
acgagcgcaa cccttgtcat tagttgccag cattaagttg gcactctaa tgagactgcc   1140
ggtgacaaac cggaggaagg tggggatgac gtcaagtcat catgccccctt atgacctggg  1200
ctacacacgt gctacaatgg acagtacaac gaggagcaag cctgcgaagg caagcgaatc  1260
tcttaaagct gttctcagtt cggactgcag tctgcaactc gactgcacga agctggaatc  1320
gctagtaatc gcggatcagc acgccgcggt gaatacgttc cgggccttg tacacaccgc   1380
ccgtcacacc atgggagtct gcaatgccca agccggtgg cctaaccttc gggaaggagc   1440
cgtctaagca gtcagattcg                                                1460
```

```
<210> SEQ ID NO 4
<211> LENGTH: 1479
<212> TYPE: DNA
<213> ORGANISM: Artificial Sequence
<220> FEATURE:
<223> OTHER INFORMATION: synthetic

<400> SEQUENCE: 4
atgggggtgg cgcgtgctat acatgcagtc gaacgagttt tggtcgatga acggtgcttg      60
cactgagatt cgacttaaaa cgagtggcgg acgggtgagt aacacgtggg taacctgccc     120
ttaagtgggg gataacattt ggaaacagat gctaataccg cataaatcca agaaccgcat     180
ggttcttggc tgaaagatgg cgcaagctat cgcttttgga tggacccgcg gcgtattagc     240
tagttggtga ggtaacggct caccaaggcg atgatacgta gccgaactga gaggttgatc     300
ggccacattg ggactgagac acggcccaaa ctcctacggg aggcagcagt agggaatctt     360
ccacaatgga cgcaagtctg atggagcaac gccgcgtgag tgaagaaggc tttcgggtcg     420
taaaactctg ttgttggaga gaatggtcg gcagagtaac tgttgtcggc gtgacggtat      480
ccaaccagaa agccacggct aactacgtgc cagcagccgc ggtaatacgt aggtggcaag     540
cgttatccgg atttattggg cgtaaagcga gcgcaggcgg ttttttaagt ctgatgtgaa     600
agccctcggc ttaaccgagg aagcgcatcg gaaactggga aacttgagtg cagaagagga     660
cagtggaact ccatgtgtag cggtgaaatg cgtagatata tggaagaaca ccagtggcga     720
aggcggctgt ctggtctgta actgacgctg aggctcgaaa gcatgggtag cgaacaggat     780
tagataccct ggtagtccat gccgtaaacg atgaatgcta ggtgttggag ggtttccgcc     840
cttcagtgcc gcagctaacg cattaagcat tccgcctggg gagtacgacc gcaaggttga     900
aactcaaagg aattgacggg ggcccgcaca agcggtggag catgtggttt aattcgaagc     960
aacgcgaaga accttaccag gtcttgacat cttttgatca cctgagagat caggtttccc    1020 cttcggggc aaaatgacag gtggtgcatg gttgtcgtca gctcgtgtcg tgagatgttg     1080
ggttaagtcc cgcaacgagc gcaacccta tgactagttg ccagcattga gttgggcact     1140
ctagtaagac tgccggtgac aaaccggagg aaggtgggga tgacgtcaaa tcatcatgcc     1200
ccttatgacc tgggctacac acgtgctaca atggatggta caacgagttg cgagaccgcg    1260
aggtcaagct aatctcttaa agccattctc agttcggact gtaggctgca actcgcctac     1320
acgaagtcgg aatcgctagt aatcgcggat cagcacgccg cggtgaatac gttcccgggc    1380
cttgtacaca ccgcccgtca caccatgaga gtttgtaaca cccgaagccg gtggcgtaac    1440
ccttttaggg agcgagccgt ctaagtgaca aaagtttcg                           1479

<210> SEQ ID NO 5
<211> LENGTH: 1001
<212> TYPE: DNA
<213> ORGANISM: Artificial Sequence
<220> FEATURE:
<223> OTHER INFORMATION: synthetic

<400> SEQUENCE: 5
atggatggcg ggtgctatac atgcagtcga acgaactctg gtattgattg gtgcttgcat      60
catgatttac atttgagtga gtggcgaact ggtgagtaac acgtgggaaa cctgcccaga     120
agcgggggat aacacctgga aacagatgct aataccgcat aacaacttgg accgcatggt     180
ccgagtttga aagatggctt cggctatcac ttttggatgg tcccgcggcg tattagctag     240
```

| | |
|---|---|
| atggtggggt aacggctcac catggcaatg atacgtagcc gacctgagag ggtaatcggc | 300 |
| cacattggga ctgagacacg gcccaaactc ctacgggagg cagcagtagg gaatcttcca | 360 |
| caatggacga aagtctgatg gagcaacgcc gcgtgagtga agaagggttt cggctcgtaa | 420 |
| aactctgttg ttaaagaaga acatatctga gagtaactgt tcaggtattg acggtattta | 480 |
| accagaaagc cacggctaac tacgtgccag cagccgcggt aatacgtagg tggcaagcgt | 540 |
| tgtccggatt tattgggcgt aaagcgagcg caggcggttt tttaagtctg atgtgaaagc | 600 |
| cttcggctca accgaagaag tgcatcggaa actgggaaac ttgagtgcag aagaggacag | 660 |
| tggaactcca tgtgtagcgg tgaaatgcgt agatatatgg aagaacacca gtggcgaagg | 720 |
| cggctgtctg gtctgtaact gacgctgagg ctcgaaagta tgggtagcaa acaggattag | 780 |
| ataccctggt agtccatacc gtaaacgatg aatgctaagt gttggagggt ttccgccctt | 840 |
| cagtgctgca gctaacgcat taagcattcc gcctggggag tacggccgca aggctgaaac | 900 |
| tcaaaggaat tgacggggc cgcacaagc ggtggagcat gtggtttaat tcgaagctac | 960 |
| gcgaagaacc ttaccaggtc ttgacatact atgcaaatct a | 1001 |

<210> SEQ ID NO 6
<211> LENGTH: 884
<212> TYPE: DNA
<213> ORGANISM: Artificial Sequence
<220> FEATURE:
<223> OTHER INFORMATION: synthetic

<400> SEQUENCE: 6

| | |
|---|---|
| gagcattcac cgcggcgttg ctgatccgcg attactagcg actccgcctt cacgcagtcg | 60 |
| agttgcagac tgcgatccga actgagaccg gttttcagcg atccgcccca cgtcaccgtg | 120 |
| tcgcaccgcg ttgtaccggc cattgtagca tgcgtgaagc cctggacgta aggggcatga | 180 |
| tgatctgacg tcatccccac cttcctccga gttgaccccg gcggtcccac atgagttccc | 240 |
| ggcatcaccc gctggcaaca tgcggcgagg gttgcgctcg ttgcgggact aacccaaca | 300 |
| tctcacgaca cgagctgacg acgaccatgc accacctgtg aaccggcccc gaagggaaac | 360 |
| cgtgtctcca cggcgatccg gcacatgtca agcccaggta aggttcttcg cgttgcatcg | 420 |
| aattaatccg catgctccgc cgcttgtgcg ggcccccgtc aatttctttg agttttagcc | 480 |
| ttgcggccgt actccccagg cgggatgctt aacgcgttgg ctccgacacg ggacccgtgg | 540 |
| aaagggcccc acatccagca tccaccgttt acggcgtgga ctaccagggt atctaatcct | 600 |
| gttcgctccc cacgctttcg ctcctcagcg tcagtgacgg cccagagacc tgccttcgcc | 660 |
| attggtgttc ttcccgatat ctacacattc caccgttaca ccgggaattc cagtctcccc | 720 |
| taccgcactc cagcccgccc gtacccgcg cagatccacc gttaggcgat ggactttcac | 780 |
| accggacgcg acgaaccgcc tacgagccct ttacgcccaa taaatccgga taacgctcgc | 840 |
| accctacgta ttaccgcggc tgctgcggcc ggccggtata ttaa | 884 |

<210> SEQ ID NO 7
<211> LENGTH: 1490
<212> TYPE: DNA
<213> ORGANISM: Artificial Sequence
<220> FEATURE:
<223> OTHER INFORMATION: synthetic

<400> SEQUENCE: 7

| | |
|---|---|
| agcgacatcc tgtcgcttag gcggctccct ccataaaggt taggccaccg actttgggcg | 60 |
| ttacaaactc ccatggtgtg acgggcggtg tgtacaaggc ccgggaacgt attcaccgcg | 120 |

```
gcatgctgat ccgcgattac tagcgattcc gacttcgtgt aggcgagttg cagcctacag      180
tccgaactga gaacggcttt aagagattag cttactctcg cgagtttgcg actcgttgta      240
ccgtccattg tagcacgtgt gtagcccagg tcataagggg catgatgatc tgacgtcgtc      300
cccaccttcc tccggtttgt caccggcagt ctcactagag tgcccaactt aatgctggca      360
actagtaaca agggttgcgc tcgttgcggg acttaaccca acatctcacg acacgagctg      420
acgacgacca tgcaccacct gtcattgcgt ccccgaaggg aacgccttat ctctaaggtt      480
agcgcaagat gtcaagacct ggtaaggttc ttcgcgtagc ttcgaattaa accacatgct      540
ccaccgcttg tgcgggcccc cgtcaattcc tttgagtttc aaccttgcgg tcgtactccc      600
caggcggagt gcttaatgcg ttagctccgg cactgaaggg cggaaaccct ccaacaccta      660
gcactcatcg tttacggcat ggactaccag ggtatctaat cctgttcgct acccatgctt      720
tcgagcctca gcgtcagttg cagaccagac agccgccttc gccactggtg ttcttccata      780
tatctacgca ttccaccgct acacatggag ttccactgtc ctcttctgca ctcaagtcgc      840
ccggtttccg atgcacttct tcggttaagc cgaaggcttt cacatcagac taagcaacc       900 gcctgcgctc gctttacgcc aataaatcc ggataacgct tgccacctac gtattaccgc      960
ggctgctggc acgtagttag ccgtgacttt ctggttggat accgtcactg cgtgaacagt     1020
tactctcacg cacgttcttc tccaacaaca gagctttacg agccgaaacc cttcttcact     1080
cacgcggtgt tgctccatca ggcttgcgcc cattgtggaa gattccctac tgctgcctcc     1140
cgtaggagta tggaccgtgt ctcagttcca ttgtggccga tcagtctctc aactcggcta     1200
tgcatcatcg ccttggtaag ccgttacctt accaactagc taatgcaccg caggtccatc     1260
ccagagtgat agccaaagcc atctttcaaa caaaagccat gcggcttttg ttgttatgcg     1320
gtattagcat ctgtttccaa atgttatccc ccgctccggg gcaggttacc tacgtgttac     1380
tcacccgtcc gccactcact ggtgatccat cgtcaatcag gtgcaagcac catcaatcag     1440
ttgggccagt gcgtacgact tgcatgtata gccaacaccg cccgatccca              1490

<210> SEQ ID NO 8
<211> LENGTH: 901
<212> TYPE: DNA
<213> ORGANISM: Artificial Sequence
<220> FEATURE:
<223> OTHER INFORMATION: synthetic

<400> SEQUENCE: 8
tatgaatagt attgtcgcag cttttccgga tttattgggc gtagagggct cgtaggcggc       60
tcgtcgcgtc cggtgtgaaa gtccatcgct taacggtgga tctgcgccgg tacgggcgg       120 gttggagtgc ggtaggggag actggaattc ccggggtaac gggggaatgt gtaaatatcg      180
ggaagaacac cgatggggaa ggcaggtctc tgggccgtca ttgacgctga ggagcgaaag      240
cgtggggagc gaacaggatt aaataccctg gtagtccacg ccgtaaacgg ggacgttgg       300 atgtggggca cgttccacgt gttccgggtc ggagctaacg cgttaagcgt cccgcctggg      360
gagtacggcc gcaaggttaa aactcaaaga aattgacggg ggcccgcaca agcggggag       420 catgcggatt aattcgatgc aacgcgaaga accttacctg gtttgacat gttcccgacg       480 acgccagaga tggcgtttcc cttcggggcg ggttcacagg tggtgcatgg tcgtcgtcag      540
ttcgtgtcgt gagatgttgg gttaagtccc gcaacgagcg caaccctcgc ccgtgttgc       600 cagcacgtta tggtgggaac tcacggggga ccgccggggt taactcggag aaaggtgggg      660
```

```
atgacgtcag atcatcatgc cccttacgtc cagggcttca cgcatgctac aatggccggt    720
tacagcggga tgcgacatgg cgacatggag cggatccctg aaaaccggtc ttcagttcgg    780
attcggagcc tgcaacccgg ctccgtgaag gcggaagtcc gctagtattc gcggatcagc    840
aacgccgcgg tgaatgcgtt tcccgggcct gtacacaccg cccgtgcggg cctaattata    900
a                                                                    901

<210> SEQ ID NO 9
<211> LENGTH: 890
<212> TYPE: DNA
<213> ORGANISM: Artificial Sequence
<220> FEATURE:
<223> OTHER INFORMATION: synthetic

<400> SEQUENCE: 9
cccgcattta ccgcgacgtt gctgattcgc gattacttag cgacttccgc cttcacgcag     60
tcgagttgca gacttgcgat ccgaacttga gaccggtttt cagggatccg ctccgcgtcg    120
ccgcgtcgca tcccgttgta ccggccattg tagcatgcgt gaagccctgg acgtaagggg    180
catgatgatc tgacgtcatc cccaccttcc tccgagttaa ccccggcggt ccccgtgag    240 ttcccggcac aatccgctgg caacacgggg cgagggttgc gctcgttgcg ggacttaacc    300
caacatctca cgacacgagc tgacgacgac catgcaccac ctgtgaaccc gccccgaagg    360
gaaaccccat ctctgggatc gtcgggaaca tgtcaagccc aggtaaggtt cttcgcgttg    420
catcgaatta atccgcatgc tccgccgctt gtgcgggccc cgtcaatttc tttgagtttt    480
tagccttgcg gccgtactcc ccaggcggga tgcttaacgc gttagctccg acacggaacc    540
cgtggaacgg gccccacatc cagcatccac cgtttacggc gtggactacc agggtatcta    600
atcctgttcg ctccccacgc tttcgctcct cagcgtcagt aacggccag agacctgcct    660 tcgccattgg tgttcttccc gatatctaca cattccaccg ttacaccggg aattccagtc    720 tccctaccg cactcaagcc cgcccgtacc cggcgcggat ccaccgttaa gcatggact    780 ttcacaccgg acgcgacgaa ccgcctacga gccctttacg cccaataatt ccggataacg    840
cttgcaccct acgtatacgc gtgtgcgccc cctattaaa aaaaaaaaa                 890

<210> SEQ ID NO 10
<211> LENGTH: 1473
<212> TYPE: DNA
<213> ORGANISM: Artificial Sequence
<220> FEATURE:
<223> OTHER INFORMATION: synthetic

<400> SEQUENCE: 10
actttgtcac ttagacggct cgctccctaa aagggttacg ccaccggctt cgggtgttac     60
aaactctcat ggtgtgacgg gcggtgtgta caaggcccgg gaacgtattc accgcggcgt    120
gctgatccgc gattactagc gattccgact tcgtgtaggc gagttgcagc ctacagtccg    180
aactgagaat ggctttaaga gattagcttg acctcgcggt ctcgcaactc gttgtaccat    240
ccattgtagc acgtgtgtag cccaggtcat aaggggcatg atgatttgac gtcatcccca    300
ccttcctccg gtttgtcacc ggcagtctta ctagagtgcc caactaaatg ctggcaacta    360
gtcataaggg ttgcgctcgt tgcgggactt aacccaacat ctcacgacac gagctgacga    420
caaccatgca ccacctgtca ttttgccccc gaagggaaaa cctgatctct caggtgatca    480
aaagatgtca agacctggta aggttcttcg cgttgcttcg aattaaacca catgctccac    540
cgcttgtgcg ggccccgtc aattccttg agtttcaacc ttgcggtcgt actccccagg    600
```

-continued

```
cggaatgctt aatgcgttag ctgcggcact gaagggcgga aaccctccaa cacctagcat     660
tcatcgttta cggcatggac taccagggta tctaatcctg ttcgctaccc atgctttcga     720
gcctcagcgt cagttacaga ccagacagcc gccttcgcca ctggtgttct tccatatatc    780
tacgcatttc accgctacac atggagttcc actgtcctct tctgcactca agtttcccag    840
tttccgatgc gcttcctcgg ttaagccgag ggctttcaca tcagacttaa aaaaccgcct    900
gcgctcgctt tacgcccaat aaatccggat aacgcttgcc acctacgtat taccgcggct    960
gctggcacgt agttagccgt ggctttctgg ttggataccg tcacgccgac aacagttact   1020
ctgccgacca ttcttctcca acaacagagt tttacgaccc gaaagccttc ttcactcacg   1080
cggcgttgct ccatcagact tgcgtccatt gtggaagatt ccctactgct gcctcccgta   1140
ggagtttggg ccgtgtctca gtcccaatgt ggccgatcaa cctctcagtt cggctacgta   1200
tcatcgcctt ggtgagccat tacctcacca actagctaat acgccgcggg tccatccaaa   1260
agcgatagct tacgccatct ttcagccaag aaccatgcgg ttcttggatc tatgcggtat   1320
tagcatctgt ttccaaatgt tatcccccac ttaagggcag gttacccacg tgttactcac   1380
ccgtccgcca ctcgttccat gttgaatctc ggtgcaagca ccgatcatca acgagaactc   1440
gttcgacttg catgtatagc acgccgcccc cac                                1473
```

PROBIOTIC FOR INHIBITING GROWTH OF *PROTEUS MIRABILIS*, AND FERMENTATION BROTH AND APPLICATION THEREOF

CROSS-REFERENCE TO RELATED APPLICATIONS

This application is a continuation of International Patent Application No. PCT/CN2021/102388, filed on Jun. 25, 2021, which claims the benefit of priority from Chinese Patent Application No. 202110530026.7, filed on May 14, 2021. The content of the aforementioned applications, including any intervening amendments thereto, is incorporated herein by reference in their entirety.

TECHNICAL FIELD

This application relates to microorganisms, and more particularly to a probiotic for inhibiting growth of *Proteus mirabilis*, and a fermentation broth and an application thereof.

BACKGROUND

Probiotics exist widely in nature, mainly from the human and animal intestines. The most common probiotics are *Lactobacillus* and *Bifidobacterium*. Probiotics are live microorganisms that are beneficial to the host through colonization, and can change the bacterial composition in a certain part of the host. It has been currently recognized that the ingestion of a certain number of live probiotics can promote the intestinal absorption, enhance human immunity and relieve allergic reactions, and thus the probiotics have been widely used in food processing and production of health care products.

Recently, several probiotic strains have been gradually isolated from the human body, and identified at the strain level. In addition, some safe functional strains, such as *Lactobacillus casei*, *Lactobacillus rhamnosus* GG (LGG) and *Bifidobacterium lactis* BB 12, have played a significant role in treating diseases including obesity, type 2 diabetes, non-alcoholic fatty liver diseases and cardiovascular and cerebrovascular diseases, exhibiting great economic potential. However, few researches have been conducted on the function of combined strains.

Atherosclerosis (AS) refers to a variety of basic diseases, including cerebral apoplexy and coronary heart disease, and is difficult to be prevented and treated. It has been recently reported that the intestinal flora may participate in the development of atherosclerosis through metabolites including trimethylamine (TMA) and trimethylamine-N-oxide (TMAO). Specifically, the ingested phosphatidylcholine and L-carnitine may be metabolized into TMA under the action of the intestinal flora, and absorbed into the blood in the intestine. The absorbed TMA is then oxidized to TMAO under the catalysis of flavin-containing monooxygenase 3 (FM03), which may further promote the development of atherosclerosis through promoting the transformation of macrophages into foam cells, leading to the occurrence of cardiovascular and cerebrovascular diseases. In addition, it has been demonstrated that the elevated concentration of TMAO in plasma is associated with the poor long-term prognosis of heart failure and chronic kidney disease, and high levels of TMAO in plasma often indicate poor prognosis. *Proteus mirabilis* is a Gram-negative opportunistic pathogen that plays an important role in promoting the production of TMA from choline and carnitine. Nonetheless, there is still no report about the inhibitory effect of probiotics on the growth of *Proteus mirabilis*. Therefore, there are still some technical barriers in reducing the occurrence of cardiovascular diseases by reducing the production of TMA using microbial therapy.

SUMMARY

An objective of the present disclosure is to provide a probiotic for inhibiting growth of *Proteus mirabilis*, and a fermentation broth and an application thereof. The probiotic can effectively inhibit the growth of *Proteus mirabilis*, reducing the generation of trimethylamine and the occurrence of cardiovascular disease. In addition, the probiotic has no adverse effect on human body.

In a first aspect, the present disclosure provides a probiotic for inhibiting growth of *Proteus mirabilis*, wherein the probiotic comprises a microorganism selected from the group consisting of *Lactobacillus rhamnosus*, *Lactobacillus fermentum*, *Lactobacillus plantarum*, *Lactobacillus casei*, *Lactobacillus acidophilus*, *Lactobacillus paracasei*, *Lactobacillus reuteri*, *Bifidobacterium animalis* subsp. *lactis*, *Bifidobacterium infantis*, *Bifidobacterium bifidum* and a combination thereof.

In some embodiments, the probiotic is a combination of the *Lactobacillus rhamnosus* and the *Lactobacillus fermentum*; a combination of the *Lactobacillus casei* and the *Bifidobacterium animalis* subsp. *lactis*; or a combination of the *Lactobacillus paracasei* and the *Bifidobacterium infantis*.

In some embodiments, the combination of the *Lactobacillus rhamnosus* and the *Lactobacillus fermentum* is obtained through inoculating a *Lactobacillus rhamnosus* culture liquid and a *Lactobacillus fermentum* culture liquid in a volume ratio of 1:1 into an MRS broth followed by anaerobic culture at 36-38° C. to an equilibrium phase;
   the combination of the *Lactobacillus casei* and the *Bifidobacterium animalis* subsp. *lactis* is obtained through inoculating a *Lactobacillus casei* culture liquid and a *Bifidobacterium animalis* subsp. *lactis* culture liquid in a volume ratio of 1:1 into an MRS broth followed by anaerobic culture at 36-38° C. to an equilibrium phase; and
   the combination of the *Lactobacillus paracasei* and the *Bifidobacterium infantis* is obtained through inoculating a *Lactobacillus paracasei* culture liquid and a *Bifidobacterium infantis* culture liquid in a volume ratio of 1:1 into an MRS broth followed by anaerobic culture at 36-38° C. to an equilibrium phase.

In some embodiments, the *Lactobacillus rhamnosus* is *Lactobacillus rhamnosus* AI-11 assigned accession CGMCC No. 21745;
   the *Lactobacillus fermentum* is *Lactobacillus fermentum* AI-25 assigned accession CGMCC No. 21746;
   the *Lactobacillus plantarum* is *Lactobacillus plantarum* AI-66 assigned accession CGMCC No. 21741;
   the *Lactobacillus casei* is *Lactobacillus casei* AI-12 assigned accession CGMCC No. 21742;
   the *Lactobacillus acidophilus* is *Lactobacillus acidophilus* AI-32 assigned accession CGMCC No. 21743;
   the *Lactobacillus paracasei* is *Lactobacillus paracasei* AI-62 assigned accession CGMCC No. 21744;
   the *Lactobacillus reuteri* is *Lactobacillus reuteri* AI-70 assigned accession CGMCC No. 21748;
   the *Bifidobacterium animalis* subsp. *lactis* is *Bifidobacterium animalis* subsp. *lactis* AI-01 assigned accession CGMCC No. 21747;

the *Bifidobacterium infantis* is *Bifidobacterium infantis* AI-20 assigned accession CGMCC No. 21779; and the *Bifidobacterium bifidum* is *Bifidobacterium bifidum* AI-91 assigned accession CGMCC No. 21780.

In a second aspect, the present disclosure provides a fermentation broth, wherein the fermentation broth is prepared through inoculating the probiotic mentioned above into a fermentation medium followed by anaerobic culture.

In some embodiments, the fermentation medium is an MRS broth; and the anaerobic culture is performed at 36-38° C. for 20-24 h.

In a third aspect, the present disclosure provides a method for inhibiting growth of *Proteus mirabilis* in a subject, comprising:

administering the probiotic or the fermentation broth to the subject.

In a fourth aspect, the present disclosure provides a method for inhibiting generation of trimethylamine in a subject, comprising:

administering the probiotic or the fermentation broth to the subject.

In a fifth aspect, the present disclosure provides a method for treating atherosclerosis in a subject in need thereof, comprising:

administering a therapeutically effective amount of the probiotic or the fermentation broth to the subject.

The beneficial effects of the present disclosure are described as follows.

The present disclosure provides a probiotic for inhibiting growth of *Proteus mirabilis*, including a *bacillus* selected from the group consisted of *Lactobacillus rhamnosus*, *Lactobacillus fermentum*, *Lactobacillus plantarum*, *Lactobacillus casei*, *Lactobacillus acidophilus*, *Lactobacillus paracasei*, *Lactobacillus reuteri*, *Bifidobacterium animalis* subsp. *lactis*, *Bifidobacterium infantis*, *Bifidobacterium bifidum* and a combination thereof. The in vitro experiment results demonstrate that each of the above-mentioned 10 strains or a combination thereof can effectively inhibit the growth of *Proteus mirabilis* in vitro. Since trimethylamine is a metabolite of *Proteus mirabilis*, the probiotic provided herein can also effectively inhibit the generation of trimethylamine, and provides a new idea for preventing and/or treating atherosclerosis related to the metabolism of trimethylamine.

In addition, the probiotic provided herein is safe, and thus can be widely used in the preparation of medicines, foods or health products for inhibiting the growth of *Proteus mirabilis* or inhibiting the production or metabolism of trimethylamine.

BRIEF DESCRIPTION OF THE DRAWINGS

FIG. 1a: *Bifidobacterium infantis* AI-20; and FIG. 1b: *Lactobacillus paracasei* AI-62;

FIG. 5a: bacteriostatic effect of supernatants with different pH; and FIG. 5b: bacteriostatic effect of buffer controls with different pH; FIG. 6a: Pepsin treatment; FIG. 6b: Trypsin treatment; FIG. 6c: Papain treatment; FIG. 6d: Proteinase K treatment; A: MRS blank control; B: 100 U/mL protease treatment; and C: 200 U/mL protease treatment.

DETAILED DESCRIPTION OF EMBODIMENTS

Deposit of Microorganisms

Figure 1A:
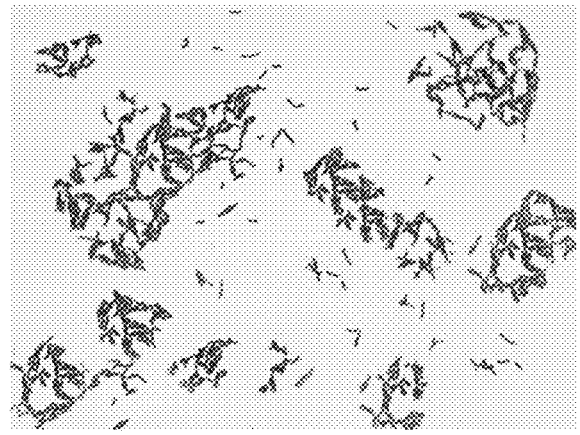
FIGS. 1a-1b show a morphology of *Bifidobacterium infantis* AI-20 and *Lactobacillus paracasei* AI-62 after Gram staining; where
Figure 1B:
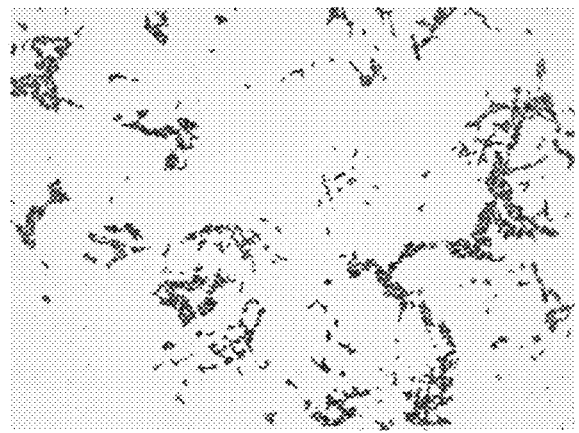
Figure 2:
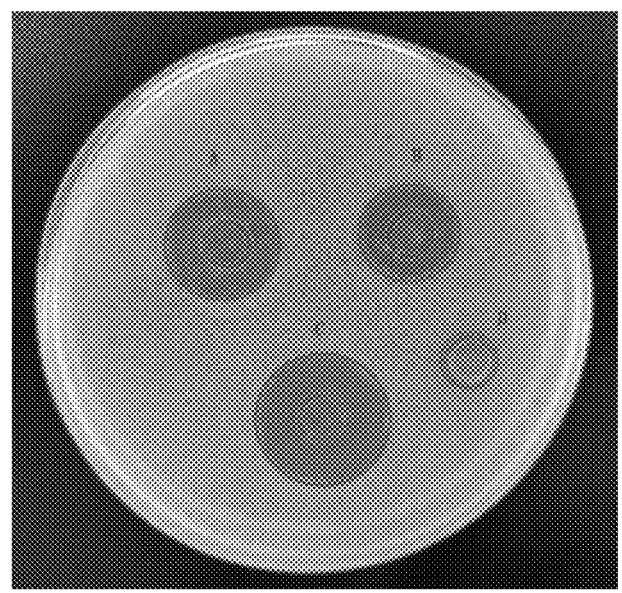
FIG. 2 shows antibacterial activity of co-cultured strains and a single strain against *Proteus mirabilis*; in which A: an inhibition zone of the *Bifidobacterium infantis* AI-20; B: an inhibition zone of the *Lactobacillus paracasei* AI-62; C: an inhibition zone of *Bifidobacterium infantis* AI-20 ✕ *Lactobacillus paracasei* AI-62; and D: MRS blank control.

The *Lactobacillus rhamnosus* AI-11 assigned CGMCC No. 21745 was deposited on Jan. 26, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Lactobacillus fermentum* AI-25 assigned CGMCC No. 21746 was deposited on Jan. 26, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Lactobacillus plantarum* AI-66 assigned CGMCC No. 21741 was deposited on Jan. 26, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Lactobacillus casei* AI-12 assigned CGMCC No. 21742 was deposited on Jan. 26, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Lactobacillus acidophilus* AI-32 assigned CGMCC No. 21743 was deposited on Jan. 26, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Lactobacillus paracasei* AI-62 assigned CGMCC No. 21744 was deposited on Jan. 26, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Lactobacillus reuteri* AI-70 assigned CGMCC No. 21748 was deposited on Jan. 26, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Bifidobacterium animalis* subsp. *lactis* AI-01 assigned CGMCC No. 21747 was deposited on Jan. 26, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Bifidobacterium infantis* AI-20 assigned CGMCC No. 21779 was deposited on Feb. 1, 2021 with China General Microbiological Culture Collection Center (CGMCC, Institute of Microbiology Chinese Academy of Sciences, Building 3, NO. 1 West Beichen Road, Chaoyang District, Beijing, 100101, China).

The *Bifidobacterium bifidum* AI-91 assigned CGMCC No. 21780 was deposited on Feb. 1, 2021 with China General Microbiological Culture Collection Center (CGMCC, Institute of Microbiology Chinese Academy of Sciences, Building 3, NO. 1 West Beichen Road, Chaoyang District, Beijing, 100101, China).

A probiotic for inhibiting growth of *Proteus mirabilis* is provided herein, which includes a microorganism selected from the group consisting of *Lactobacillus rhamnosus, Lactobacillus fermentum, Lactobacillus plantarum, Lactobacillus casei, Lactobacillus acidophilus, Lactobacillus paracasei, Lactobacillus reuteri, Bifidobacterium animalis* subsp. *lactis, Bifidobacterium infantis, Bifidobacterium bifidum* and a combination thereof.

In some embodiments, the probiotic includes a combination of the *Lactobacillus rhamnosus* and the *Lactobacillus fermentum*, a combination of the *Lactobacillus casei* and the *Bifidobacterium animalis* subsp. *lactis*, or a combination of the *Lactobacillus paracasei* and the *Bifidobacterium infantis*. The combination of the *Lactobacillus rhamnosus* and the *Lactobacillus fermentum* is obtained through inoculating a *Lactobacillus rhamnosus* culture liquid and a *Lactobacillus fermentum* culture liquid in a volume ratio of 1:1 into an MRS broth followed by anaerobic culture at 36-38° C. to an equilibrium phase. The combination of the *Lactobacillus casei* and the *Bifidobacterium animalis* subsp. *lactis* is obtained through inoculating a *Lactobacillus casei* culture liquid and a *Bifidobacterium animalis* subsp. *lactis* culture liquid in a volume ratio of 1:1 into an MRS broth followed by anaerobic culture at 36-38° C. to an equilibrium phase. The combination of the *Lactobacillus paracasei* and the *Bifidobacterium infantis* is obtained through inoculating a *Lactobacillus paracasei* culture liquid and a *Bifidobacterium infantis* culture liquid in a volume ratio of 1:1 into an MRS broth followed by anaerobic culture at 36-38° C. to an equilibrium phase, where a ratio of the number of colonies of the *Lactobacillus paracasei* to the number of colonies of the *Bifidobacterium infantis* is (1-5):(18-20), preferably 1:19. The *Lactobacillus rhamnosus, Lactobacillus fermentum, Lactobacillus plantarum, Lactobacillus casei, Lactobacillus acidophilus, Lactobacillus paracasei, Lactobacillus reuteri, Bifidobacterium animalis* subsp. *lactis, Bifidobacterium infantis, Bifidobacterium bifidum* can be cultured using the method well known in the art, and the specific operation is not specifically limited herein.

Strains of the above 10 kinds of *bacilli* are not specifically limited. In this embodiment, the *Lactobacillus rhamnosus* is *Lactobacillus rhamnosus* AI-11 assigned accession CGMCC No. 21745; the *Lactobacillus fermentum* is *Lactobacillus fermentum* AI-25 assigned accession CGMCC No. 21746; the *Lactobacillus plantarum* is *Lactobacillus plantarum* AI-66 assigned accession CGMCC No. 21741; the *Lactobacillus casei* is *Lactobacillus casei* AI-12 assigned accession CGMCC No. 21742; the *Lactobacillus acidophilus* is *Lactobacillus acidophilus* AI-32 assigned accession CGMCC No. 21743; the *Lactobacillus paracasei* is *Lactobacillus paracasei* AI-62 assigned accession CGMCC No. 21744; the *Lactobacillus reuteri* is *Lactobacillus reuteri* AI-70 assigned accession CGMCC No. 21748; the *Bifidobacterium animalis* subsp. *lactis* is *Bifidobacterium animalis* subsp. *lactis* AI-01 assigned accession CGMCC No. 21747; the *Bifidobacterium infantis* is *Bifidobacterium infantis* AI-20 assigned accession CGMCC No. 21779; and the *Bifidobacterium bifidum* is *Bifidobacterium bifidum* AI-91 assigned accession CGMCC No. 21780.

The in-vitro bacteriostatic experiment shows that the above 10 kinds of *bacilli* all have the activity of inhibiting the growth of *Proteus mirabilis*. Therefore, a single probiotic strain can inhibit the growth of *Proteus mirabilis*. The experiment results also demonstrate that a combination of two or more *bacilli* has a higher activity of inhibiting the growth of *Proteus mirabilis* than a single *bacillus*.

A fermentation broth of the probiotic for inhibiting growth of *Proteus mirabilis* is prepared as follows.

The probiotic is inoculated into a fermentation medium and subjected to anaerobic culture to obtain the fermentation broth.

The culture of the *Lactobacillus rhamnosus, Lactobacillus fermentum, Lactobacillus plantarum, Lactobacillus casei, Lactobacillus acidophilus, Lactobacillus paracasei, Lactobacillus reuteri, Bifidobacterium animalis* sub sp. *lactis, Bifidobacterium infantis, Bifidobacterium bifidum* can be performed using the method well known in the art, and is not specifically limited.

In some embodiments, the fermentation medium is an MRS broth. An inoculation amount is 0.5%-3%, preferably 1%. The anaerobic culture is performed at 36-38° C. for 20-24 h, preferably 37° C. for 21-23 hours. More preferably, the anaerobic culture is performed for 22 h. In this embodiment, a strain stored at −20° C. in a glycerol stock tube is inoculated into a normal MRS broth followed by 2 to 3 times of transfer and activation to obtain a culture liquid. The culture liquid is then inoculated into another MRS broth at an inoculation amount of 1%, and cultured anaerobically at 37° C. to an equilibrium phase (20-24 h). When the probiotic is composed of two kinds of strains, the culture liquids of the two strains are inoculated into an MRS broth in a volume ratio of 1:1, and a total inoculation amount is 1%.

In this embodiment, during the fermentation, a bacteriostatic active substance of the probiotic is secreted into the fermentation broth during the growth of the probiotic, and a bacteriostatic activity of the fermentation broth reaches the maximum after 12-16 h. The bacteriostatic active substance in the fermentation broth can withstand high temperature and even retain a high activity of inhibiting the growth of *Proteus mirabilis* at 100° C.

In view of the fact that the probiotic and the fermentation broth thereof both have the activity of inhibiting the growth of *Proteus mirabilis*, the probiotic and the fermentation broth are further used in the preparation of a reagent for inhibiting the growth of *Proteus mirabilis*.

In view of the fact that the probiotic and the fermentation broth thereof have the activity of inhibiting the growth of *Proteus mirabilis*, and the *Proteus mirabilis* has the ability to produce trimethylamine, the probiotic and the fermentation broth are further used in the preparation of a drug for inhibiting the generation of trimethylamine.

In view of the fact that the probiotic and the fermentation broth thereof have the activity of inhibiting the growth of *Proteus mirabilis*, and the *Proteus mirabilis* is capable of producing trimethylamine, whose metabolism may cause atherosclerosis, the probiotic and the fermentation broth are further used in the preparation of a drug for preventing and/or treating atherosclerosis.

In view of the fact that the probiotic and the fermentation broth thereof have the activity of inhibiting the growth of *Proteus mirabilis*, and the probiotic can tolerate pH 1.5-2.5 and a bile salt concentration of 0.3%, an oral product for inhibiting the growth of *Proteus mirabilis* is provided, which includes the probiotic or the fermentation broth thereof.

The probiotic for inhibiting the growth of *Proteus mirabilis*, and the fermentation broth and application thereof will be further described below in detail with reference to the embodiments, which are not intended to limit the scope of the present disclosure.

EXAMPLE 1

A method for screening and identifying *Lactobacillus rhamnosus* AI-11, *Lactobacillus fermentum* AI-25, *Lactobacillus acidophilus* AI-32, *Lactobacillus casei* AI-12, *Lactobacillus plantarum* AI-66, *Bifidobacterium animalis* sub sp. *lactis* AI-01, *Lactobacillus reuteri* AI-70, *Bifidobacterium bifidum* AI-91, *Bifidobacterium infant* AI-20 and *Lactobacillus paracasei* AI-62 was provided herein.

Single colony of the *Lactobacillus rhamnosus* AI-11: white to translucent; raised surface and regular round edge; and short straight rods with regular arrangement.

Single colony of the *Lactobacillus fermentum* AI-25: transparent; raised surface and regular round edge; and straight rods with different lengths and regular arrangement.

Single colony of the *Lactobacillus acidophilus* AI-32: transparent; flat surface and irregular star-shaped rough edge; and straight rods with different lengths and irregular arrangement.

Single colony of the *Lactobacillus casei* AI-12: white to translucent; flat surface and irregular star-shaped rough edge; and straight rods with different lengths and regular arrangement.

Single colony of the *Lactobacillus plantarum* AI-66: white; raised surface and regular round edge; and short straight rods with regular arrangement.

Single colony of the *Bifidobacterium animalis* subsp. *lactis* AI-01: white to translucent; raised surface and regular round edge; short straight rods with one end bifurcated sometimes; and regular arrangement.

Single colony of the *Lactobacillus reuteri* AI-70: transparent; flat surface and irregular star-shaped rough edge; and straight rods with different lengths and regular arrangement.

Single colony of the *Bifidobacterium bifidum* AI-91: white to translucent; raised surface and regular round edge; short and thin straight rods with top end bifurcated sometimes; and irregular arrangement.

Single colony of the *Bifidobacterium infantis* AI-20: white to translucent; raised and moist surface and regular round edge; short rods with different lengths and regular arrangement.

Single colony of the *Lactobacillus paracasei* AI-62: white to translucent; raised and moist surface and regular round edge; and short straight rods with regular arrangement.

Through the 16S rDNA molecular identification, the 16S rDNA sequences of the strains AI-11, AI-25, AI-32, AI-12, AI-66, AI-01, AI-70, AI-91, AI-20 and AI-62 (respectively shown in SEQ ID NOs: 1-10) were respectively demonstrated to have the highest homology (up to 100%) with *Lactobacillus rhamnosus*, *Lactobacillus fermentum*, *Lactobacillus acidophilus*, *Lactobacillus casei*, *Lactobacillus plantarum*, *Bifidobacterium animalis* subsp. *lactis*, *Lactobacillus reuteri*, *Bifidobacterium bifidum*, *Bifidobacterium infantis* and *Lactobacillus infantis paracasei*. According to the morphology characteristics and the results of molecular identification, the strains AI-11, AI-25, AI-32, AI-12, AI-66, AI-01, AI-70, AI-91, AI-20 and AI-62 were determined to pertain to *Lactobacillus rhamnosus*, *Lactobacillus fermentum*, *Lactobacillus acidophilus*, *Lactobacillus casei*, *Lactobacillus plantarum*, *Bifidobacterium animalis* subsp. *lactis*, *Lactobacillus reuteri*, *Bifidobacterium bifidum*, *Bifidobacterium infantis* and *Lactobacillus paracasei*, respectively.

The above ten strains were deposited, where the *Lactobacillus rhamnosus* AI-11 was assigned accession CGMCC No. 21745; the *Lactobacillus fermentum* AI-25 was assigned accession CGMCC No. 21746; the *Lactobacillus acidophilus* AI-32 was assigned accession CGMCC No. 21743; the *Lactobacillus casei* AI-12 was assigned accession CGMCC No. 21742; the *Lactobacillus plantarum* AI-66 was assigned accession CGMCC No. 21741; the *Bifidobacterium animalis* subsp. *lactis* AI-01 was assigned accession CGMCC No. 21747; the *Lactobacillus reuteri* AI-70 was assigned accession CGMCC No. 21748; the *Bifidobacterium bifidum* AI-91 was assigned accession CGMCC No. 21780; the *Bifidobacterium infantis* AI-20 was assigned accession CGMCC No. 21779; and the *Lactobacillus paracasei* AI-62 was assigned accession CGMCC No. 21744.

EXAMPLE 2

Safety Evaluation of Strains

The *Bifidobacterium infantis* AI-20 strain and the *Lactobacillus paracasei* AI-62 strain that were stored at −20° C. in a glycerol tube were respectively inoculated into a normal MRS broth followed by 2 to 3 times of transfer and activation. The activated *Bifidobacterium infantis* AI-20 culture liquid and the activated *Lactobacillus paracasei* AI-62 culture liquid were inoculated in a volume ratio of 1:1 into an MRS broth at a total inoculation amount of 1%, and then cultured anaerobically at 37° C. to an equilibrium phase to obtain a probiotic combination of the *Bifidobacterium infantis* AI-20 and the *Lactobacillus paracasei* AI-62. Similarly, a probiotic combination (*Lactobacillus rhamnosus* AI-11 ⊗ *Lactobacillus fermentum* AI-25) of the *Lactobacillus rhamnosus* AI-11 and the *Lactobacillus fermentum* AI-25 and a probiotic combination (*Lactobacillus casei* AI-12 ⊗ *Bifidobacterium animalis* subsp. *lactis* AI-01) of the *Lactobacillus casei* AI-12 and the *Bifidobacterium animalis* sub sp. *lactis* AI-01 were prepared.

The prepared three probiotic combinations (*Lactobacillus rhamnosus* AI-11 ⊗ *Lactobacillus fermentum* AI-25, *Lactobacillus casei* AI-12 ⊗ *Bifidobacterium animalis* subsp. *lactis* AI-01 and *Bifidobacterium infantis* AI-20 ⊗ *Lactobacillus paracasei* AI-62), each for 0.5 mL, were spread evenly on a surface of an MRS agar plate, respectively, and dried. Then the gentamicin, vancomycin, kanamycin, clindamycin, streptomycin, ampicillin, tetracycline, erythromycin and chloromycetin susceptibility discs were attached to the surface of the MRS agar plate. Subsequently, the MRS agar plate was cultured in an incubator at 37° C. for 24-48 h to observe the growth of the strains. If there was an obvious transparent circle around the susceptibility disk, a diameter of the transparent circle was measured with a ruler to judge whether the tested strain had antibiotic susceptibility. *Staphylococcus aureus* was selected as a quality control strain for the antibiotic susceptibility test. Whether the tested strains have resistance to various antibiotics was determined according to the relevant standards (Table 1) formulated by the American Clinical and Laboratory Standards Institute (CLSI).

TABLE 1

Content of antibiotics and judgment criteria of antibiotic resistance

| Antibiotic | Content (μg/disc) | Diameter of inhibition zone (mm) | | |
|---|---|---|---|---|
| | | Resistant (R) | Intermediate (I) | Susceptible (S) |
| Ampicillin | 10 | ≤12 | 13-17 | ≥18 |
| Vancomycin | 30 | ≤12 | 13-17 | ≥18 |
| Gentamicin | 120 | ≤12 | 13-17 | ≥18 |
| Kanamycin | 30 | ≤12 | 13-17 | ≥18 |
| Streptomycin | 10 | ≤12 | 13-17 | ≥18 |
| Erythromycin | 15 | ≤13 | 14-22 | ≥23 |
| Tetracycline | 30 | ≤14 | 15-18 | ≥19 |
| Chloromycetin | 30 | ≤12 | 13-17 | ≥18 |
| Clindamycin | 2 | ≤14 | 15-20 | ≥21 |

TABLE 2

Results of Kirby-Bauer disk diffusion susceptibility test

| Strains for antibiotic susceptibility assessment | Lactobacillus rhamnosus AI-11 ※ Lactobacillus fermentum AI-25 | Bifidobacterium animalis subsp. lactis AI-01 ※ Lactobacillus casei AI-12 | Bifidobacterium infantis AI-20 ※ Lactobacillus paracasei AI-62 |
|---|---|---|---|
| Ampicillin | S | S | S |
| Vancomycin | / | I | S |
| Gentamicin | S | S | S |
| Kanamycin | S | I | S |
| Streptomycin | I | I | S |
| Erythromycin | S | S | I |
| Tetracycline | S | S | S |
| Chloromycetin | S | S | S |
| Clindamycin | S | S | S |

Note: "S" indicated that the strain was susceptible to the antibiotic; "I" indicated that the strain exhibited intermediate susceptibility to the antibiotic; "R" indicated that the strain was resistant to the antibiotic; and "/" indicated that the strain did not require a safety assessment for the antibiotic.

According to the results of Kirby-Bauer disk diffusion susceptibility test shown in Table 2, the three probiotic combinations were highly sensitive to the above nine antibiotics, which indicated that the three probiotic combinations had high safety.

EXAMPLE 3

Proportion of Individual Strains After Co-Cultured to Equilibrium Phase

The *Bifidobacterium infantis* AI-20 and the *Lactobacillus paracasei* AI-62 that were stored at −20° C. in a glycerol tube were respectively inoculated into a normal MRS broth and activated at 37° C. followed by 2 to 3 times of transfer and activation. The activated *Bifidobacterium infantis* AI-20 culture liquid and the activated *Lactobacillus paracasei* AI-62 culture liquid were inoculated in a volume ratio of 1:1 into a tube at a total inoculation amount of 1%, cultured at 37° C. for 24-48 h and counted for the viable cells. Half of the plates for viable count were anaerobically cultured at 37° C., and the other half was aerobically cultured at 37° C. After 48 h, the proportion of viable bacteria was observed.

The results showed that in the case of an inoculation volume ratio of 1:1, a final ratio of the number of the colonies of the *Bifidobacterium infantis* AI-20 to the number of the colonies of the *Lactobacillus paracasei* AI-62 was 1:19 after the co-culture.

EXAMPLE 4

The probiotic combination of the *Bifidobacterium infantis* AI-20 and the *Lactobacillus paracasei* AI-62 (*Bifidobacterium infantis* AI-20 ※ *Lactobacillus paracasei* AI-62), the probiotic combination (*Lactobacillus rhamnosus* AI-11 ※ *Lactobacillus fermentum* AI-25) of the *Lactobacillus rhamnosus* AI-11 and the *Lactobacillus fermentum* AI-25 and the probiotic combination (*Lactobacillus casei* AI-12 ※ *Bifidobacterium animalis* sub sp. *lactis* AI-01) of the *Lactobacillus casei* AI-12 and the *Bifidobacterium animalis* subsp. *lactis* AI-01 were prepared according to the method in Example 2 for the in vitro inhibition experiment of *Proteus mirabilis*. Moreover, the *Lactobacillus rhamnosus* AI-11, the *Lactobacillus fermentum* AI-25, the *Lactobacillus plantarum* AI-66, the *Lactobacillus casei* AI-12, the *Lactobacillus acidophilus* AI-32, the *Lactobacillus paracasei* AI-62, the *Lactobacillus reuteri* AI-70, the *Bifidobacterium animalis* subsp. *lactis* AI-01, the *Bifidobacterium infantis* AI-20 and the *Bifidobacterium bifidum* AI-91 were respectively tested by the general Oxford cup assay to analyze the inhibitory activity against *Proteus mirabi*.

TABLE 3

Experimental results of inhibitory activity of single strain against Proteus mirabilis

| Strain | Diameter of inhibition zone (mm) | | | | |
|---|---|---|---|---|---|
| | 1 | 2 | 3 | 4 | Mean |
| Lactobacillus rhamnosus AI-11 | 12 | 11 | 13 | 13 | 13 |
| Lactobacillus fermentum AI-25 | 13 | 14 | 13 | 13 | 13 |
| Lactobacillus acidophilus AI-32 | 18 | 19 | 19 | 18 | 19 |
| Lactobacillus paracasei AI-62 | 18 | 19 | 19 | 18 | 18 |
| Lactobacillus casei AI-12 | 16 | 17 | 18 | 17 | 17 |
| Lactobacillus plantarum AI-66 | 20 | 19 | 19 | 20 | 20 |
| Lactobacillus reuteri AI-70 | 14 | 13 | 14 | 10 | 13 |
| Bifidobacterium animalis subsp. lactis AI-01 | 17 | 18 | 17 | 18 | 18 |
| Bifidobacterium infantis AI-20 | 17 | 16 | 15 | 16 | 16 |
| Bifidobacterium bifidum AI-91 | 17 | 17 | 18 | 18 | 18 |

TABLE 4

Comparison of single strain and co-cultured strains in the inhibitory activity against Proteus mirabilis

| Strain | Diameter of inhibition zone (mm) | | | | |
|---|---|---|---|---|---|
| | 1 | 2 | 3 | 4 | Mean |
| Lactobacillus rhamnosus AI-11 | 12 | 11 | 13 | 13 | 13 |
| Lactobacillus fermentum AI-25 | 13 | 14 | 13 | 13 | 13 |
| Lactobacillus rhamnosus AI-11 ※Lactobacillus fermentum AI-25 | 17 | 17 | 18 | 19 | 18 |
| Lactobacillus casei AI-12 | 16 | 17 | 18 | 17 | 17 |
| Bifidobacterium animalis subsp. lactis AI-01 | 17 | 18 | 17 | 18 | 18 |
| Lactobacillus casei AI-12※ Bifidobacterium animalis subsp. lactis AI-01 | 21 | 21 | 22 | 22 | 22 |

TABLE 4-continued

Comparison of single strain and co-cultured
strains in the inhibitory activity against Proteus mirabilis

| Strain | Diameter of inhibition zone (mm) | | | | |
|---|---|---|---|---|---|
| | 1 | 2 | 3 | 4 | Mean |
| Lactobacillus paracasei AI-62 | 18 | 19 | 19 | 18 | 18 |
| Bifidobacterium infantis AI-20 | 17 | 16 | 15 | 16 | 16 |
| Bifidobacterium infantis AI-20 ※Lactobacillus paracasei AI-62 | 24 | 21 | 22 | 22 | 22 |

The results showed that the above six strains all could inhibit *Proteus mirabilis*, and the co-cultured strains *Lactobacillus rhamnosus* AI-11 ※ *Lactobacillus fermentum* AI-25, *Lactobacillus casei* AI-12 ※ *Bifidobacterium animalis* subsp. *lactis* AI-01 and *Bifidobacterium infantis* AI-20 ※ *Lactobacillus paracasei* AI-62 were superior to the single strain in the inhibitory activity against *Proteus mirabilis*.

EXAMPLE 5

Changes of Bacteriostatic Activity of Co-Cultured Strains During Fermentation

The *Bifidobacterium infantis* AI-20 and the *Lactobacillus paracasei* AI-62 that were stored at −20° C. in a glycerol tube were respectively inoculated into a normal MRS broth followed by 2 to 3 times of transfer and activation. The activated *Bifidobacterium infantis* AI-20 culture liquid and the activated *Lactobacillus paracasei* AI-62 culture liquid were inoculated into six tubes containing MRS broth in a volume ratio of 1:1 and a total inoculation amount of 1%, and anaerobically cultured at 37° C. One tube of the co-cultured strains was taken out every 4 h to measure the pH value, and then centrifuged to obtain a supernatant for measuring the bacteriostatic activity against *Proteus mirabilis*.

Figure 3:
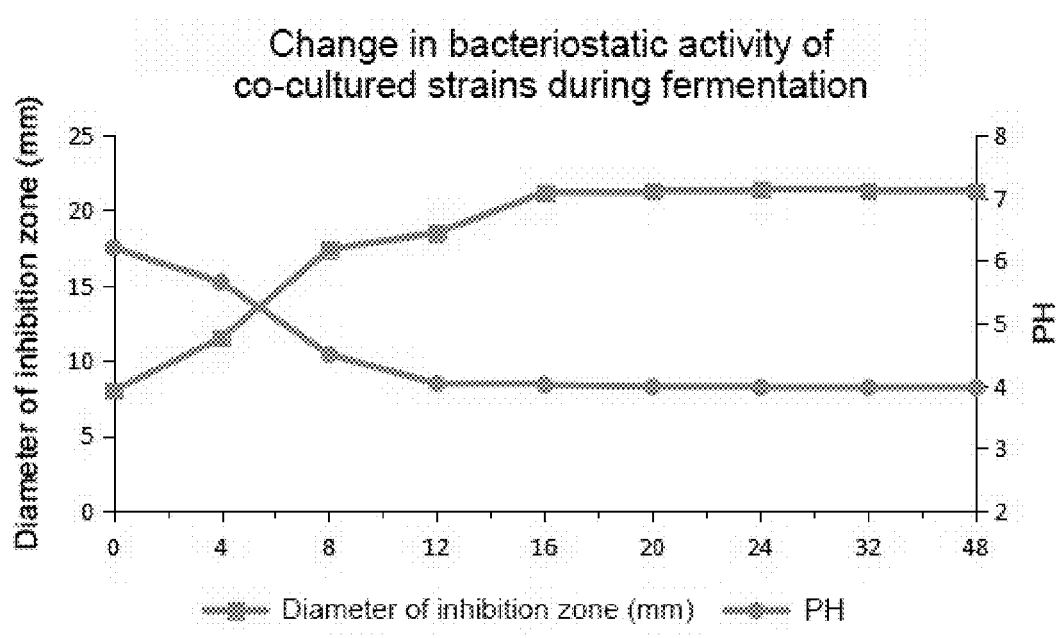
FIG. 3 shows a change in bacteriostatic activity of a probiotic combination of the *Bifidobacterium infantis* AI-20 and the *Lactobacillus paracasei* AI-62 during fermentation.

It can be observed from FIG. 3 that the secretion of the bacteriostatic substance reached the maximum at the $12^{th}$-$16^{th}$ h during the fermentation process, and the bacteriostatic effect tended to be stable with the extension of the fermentation time. At the same time, the pH of the supernatant changed greatly in the first 16 h of the fermentation process, and then with the extension of fermentation time, the change was weakened and the pH tended to be stable.

EXAMPLE 6

Effect of Heat Treatment on the Bacteriostatic Activity of the Probiotic

A probiotic combination of the *Bifidobacterium infantis* AI-20 and the *Lactobacillus paracasei* AI-62 (a volume ratio of the *Bifidobacterium infantis* AI-20 culture liquid strain to the *Lactobacillus paracasei* AI-62 culture liquid was 1:1, and a bacterial count ratio was 1:19), a probiotic combination of the *Lactobacillus rhamnosus* AI-11 and the *Lactobacillus fermentum* AI-25 (a volume ratio was 1:1) and a probiotic combination of the *Bifidobacterium animalis* subsp. *lactis* AI-01 and the *Lactobacillus casei* AI-12 (a volume ratio was 1:1) were prepared according to the method used in Example 2.

The three probiotic combinations prepared above were inoculated into six tubes containing MRS broth with an inoculum amount of 1%, respectively, and anaerobically cultured at 37° C. for about 24 h to an equilibrium phase to collect a fermentation broth. The fermentation broth was centrifuged to obtain a supernatant. The obtained six supernatant samples were subjected to water bath treatment at 50° C., 60° C., 70° C., 80° C., 90° C. and 100° C. for 20 min, respectively, and then tested for the inhibitory activity against the *Proteus mirabilis* according to the general Oxford cup assay.

TABLE 5

Effect of heat treatment on the bacteriostatic activity
of the samples (Diameter of inhibition zone, mm)

| Temperature | 37° C. | 50° C. | 60° C. | 80° C. | 100° C. |
|---|---|---|---|---|---|
| Bifidobacterium infantis AI-20·※·Lactobacillus paracasei AI-62 | 21.8 | 20.5 | 20.7 | 21.9 | 21.6 |
| Lactobacillus rhamnosus AI-11·※·Lactobacillus fermentum AI-25 | 17.8 | 17.3 | 17.5 | 17.9 | 17.8 |
| Bifidobacterium animalis subsp. lactis AI-01·※·Lactobacillus casei AI-12 | 21.6 | 21.5 | 21.6 | 21.4 | 21.8 |

Figure 4:
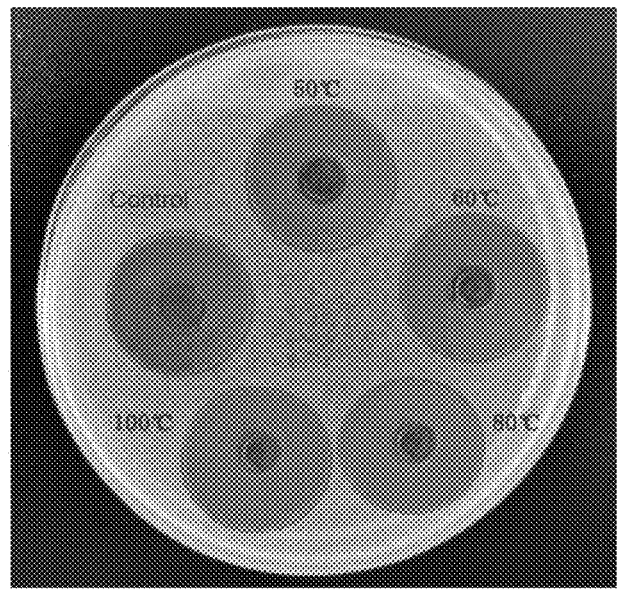
FIG. 4 shows an effect of heat treatment on the bacteriostatic activity of the probiotic.

It can be observed from Table 5 and FIG. 4 that there was no significant difference in the bacteriostatic activity of the fermentation broth against *Proteus mirabilis* before and after treatment at 50-100° C. Therefore, the bacteriostatic substance was not sensitive to heat, and would not be a macromolecular protein.

EXAMPLE 7

Effect of pH on the Bacteriostatic Activity of the Probiotic

The three probiotic combinations as shown Table 6 were prepared according to the method used in Example 2, the obtained three supernatant samples was obtained after centrifugation, and the pH of each supernatant sample was respectively adjusted to 2.0, 3.0, 4.0, 5.0, 6.0, 7.0, 8.0 using a concentrated hydrochloric acid and a concentrated sodium hydroxide. At the same time, a phosphate buffer was set as a control. The treated supernatant samples were tested for the inhibitory activity against the *Proteus mirabilis* according to the general Oxford cup assay.

TABLE 6

Effect of pH on the bacteriostatic activity of the samples
(Diameter of inhibition zone, mm)

| pH | 2.0 | 3.0 | 4.0 | 5.0 | 6.0 |
|---|---|---|---|---|---|
| Phosphate buffer | 13.8 | — | — | — | — |
| Bifidobacterium infantis AI-20·※·Lactobacillus paracasei AI-62 | 27.1 | 25.1 | 21.2 | 19.8 | — |
| Lactobacillus rhamnosus AI-11·※·Lactobacillus fermentum AI-25 | 24.8 | 22.0 | 17.9 | 16.4 | — |
| Bifidobacterium animalis subsp. lactis AI-01·※·Lactobacillus casei AI-12 | 26.7 | 24.8 | 21.1 | 19.5 | — |

Figure 5A:
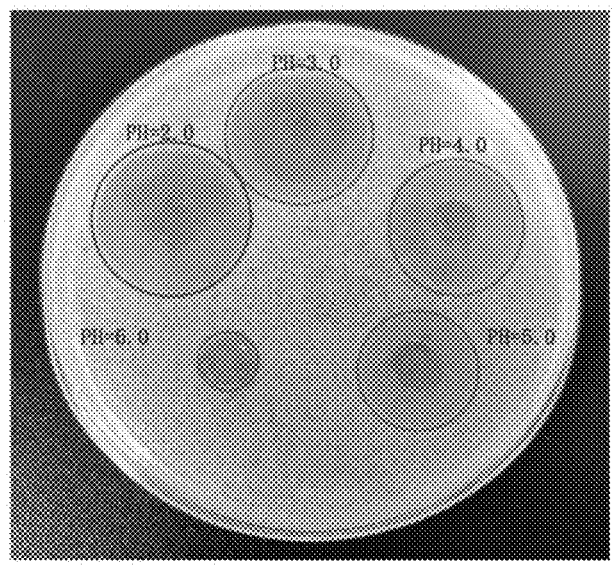
FIGS. 5a-5b show an effect of pH on the bacteriostatic activity of the probiotic; where
Figure 5B:
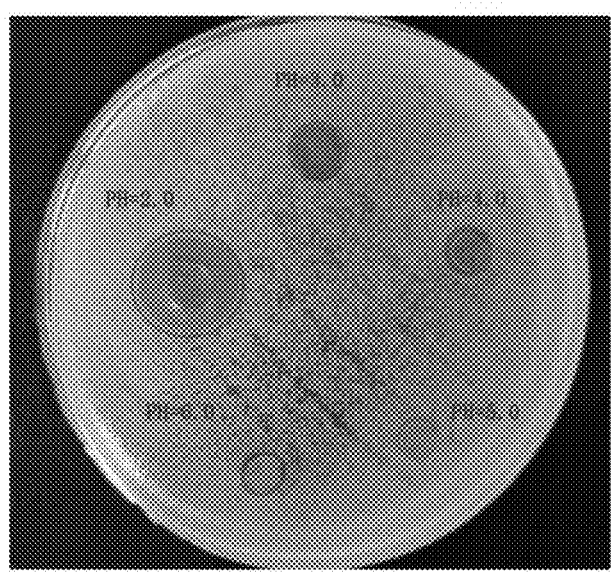
Figure 6A:
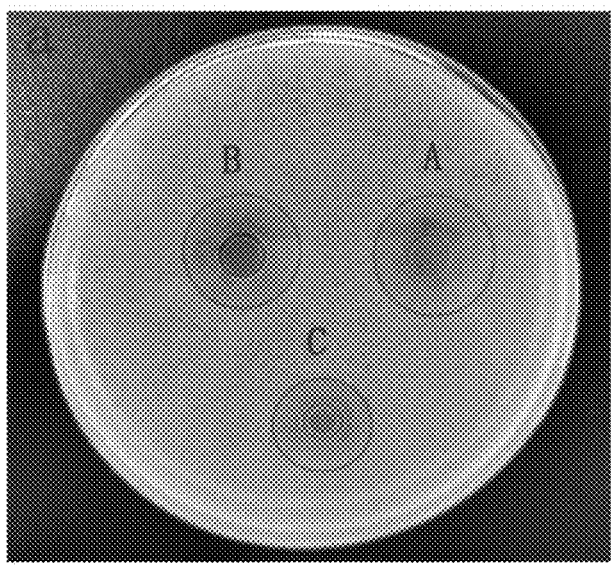
FIGS. 6a-6d show an effect of protease pretreatment on the bacteriostatic activity of the probiotic; where
Figure 6B:
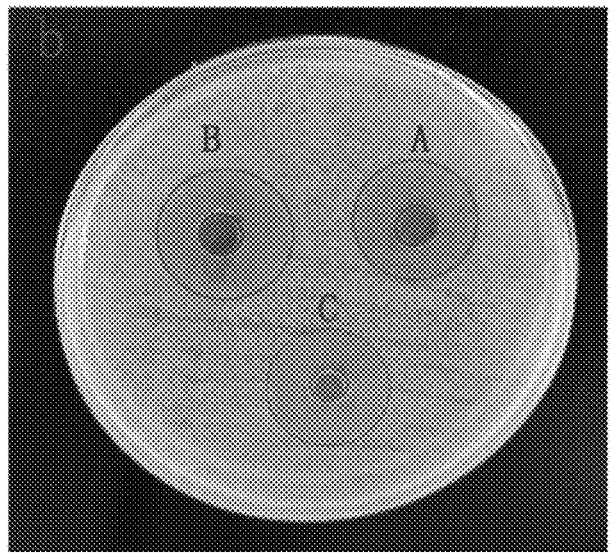
Figure 6C:
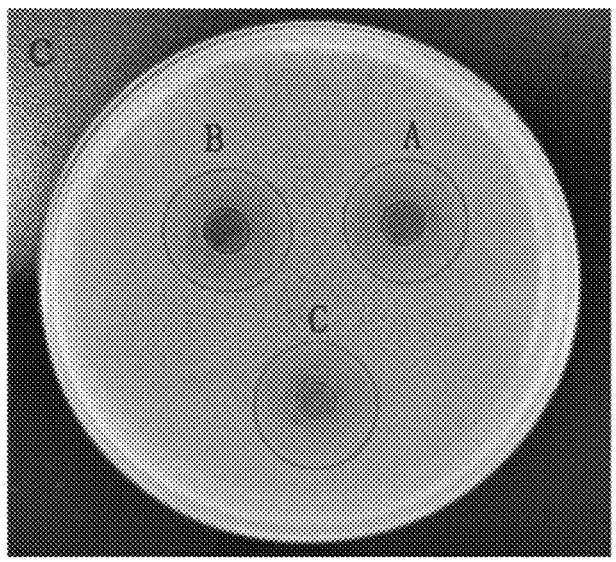
Figure 6D:
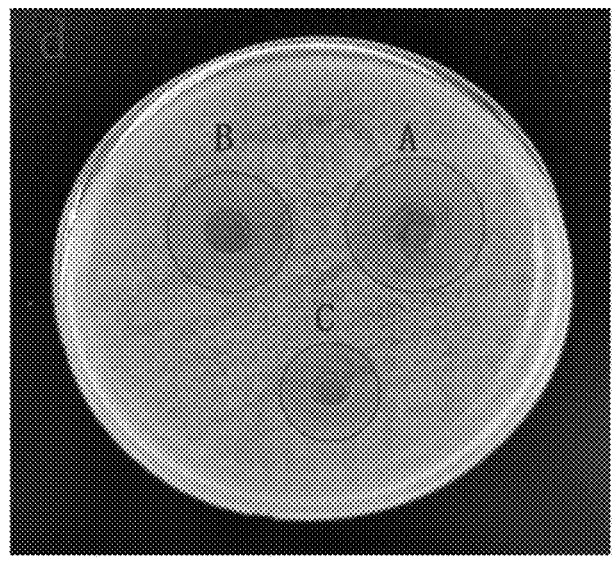

It can be observed from Table 6 and FIG. 5 that when the pH of the supernatant samples was lower than 5.0, the supernatant samples had bacteriostatic activity and the diameter of the inhibition zone gradually increased with the decrease of pH; when the pH of the supernatant was higher than 5.0, the supernatant samples had no bacteriostatic activity; and the phosphate-hydrochloric acid buffer in the control group showed weak bacteriostatic effect only when the pH reached 2.0. Therefore, low pH was a necessary condition to produce bacteriostatic effect, and the effect of some bacteriostatic substances was enhanced at low pH.

EXAMPLE 8

Effect of Protease Pretreatment on the Bacteriostatic Activity of the Probiotic

The probiotic combination of the *Bifidobacterium infantis* AI-20 and the *Lactobacillus paracasei* AI-62 was prepared according to the method used in Example 2, and was then centrifuged to obtain a supernatant sample. The supernatant sample was respectively adjusted to the optimum pH for pepsin (2.0), trypsin (8.0), proteinase K (8.0) and papain (7.0), added with the corresponding enzymes to adjust the enzyme concentration to 0 U/mL, 100 U/mL and 200 U/mL, placed at an optimal treatment temperature for the pepsin (37° C.), the trypsin (37° C.), the proteinase K (37° C.) and the papain (50° C.) overnight, subjected to a boiling water bath at 100° C. for 5-10 min, and then tested for the inhibitory activity against the *Proteus mirabilis* according to the general Oxford cup assay.

TABLE 7

Effect of protease pretreatment on the bacteriostatic activity of the samples (Diameter of inhibition zone, mm)

| | Protease | | | | | | | | | | | |
|---|---|---|---|---|---|---|---|---|---|---|---|---|
| | Pepsin | | | Trypsin | | | Papain | | | Proteinase K | | |
| | Enzyme concentration (U/mL) | | | | | | | | | | | |
| | 0 | 100 | 200 | 0 | 100 | 200 | 0 | 100 | 200 | 0 | 100 | 200 |
| *Bifidobacterium infantis* AI-20·X·*Lactobacillus paracasei* AI-62 | 22.6 | 20.7 | 18.4 | 22.4 | 22.0 | 22.0 | 21.2 | 21.0 | 20.8 | 23.8 | 20.5 | 18.4 |

It can be observed from Table 7 and FIG. 6 that after being treated with the trypsin and the papain, the fermentation broth prepared from the probiotic combination of the *Bifidobacterium infantis* AI-20 and the *Lactobacillus paracasei* AI-62 had no significant change in the bacteriostatic activity; and after the treatment with the pepsin and the proteinase K, the bacteriostatic activity of the fermentation broth decreased with the increase of the amount of the protease. Therefore, the bacteriostatic substance included some substances sensitive to protease, which may be small molecular polypeptides or bacteriocins.

The embodiments mentioned above are merely illustrative of the present disclosure, and not intended to limit the scope of this disclosure. It should be noted that improvements and modifications made by those skilled in the art without departing from the spirit of the present disclosure should fall within the scope of the present disclosure defined by the appended claims.

What is claimed is:

1. A method for inhibiting growth of *Proteus mirabilis* in a subject, comprising:
   administering a probiotic to the subject;
   wherein the probiotic comprises a microorganism selected from the group consisting of *Lactobacillus rhamnosus, Lactobacillus fermentum, Lactobacillus plantarum, Lactobacillus casei, Lactobacillus acidophilus, Lactobacillus paracasei, Lactobacillus reuteri, Bifidobacterium animalis* subsp. *lactis, Bifidobacterium infantis, Bifidobacterium bifidum* and a combination thereof; and
   the *Lactobacillus rhamnosus* is *Lactobacillus rhamnosus* AI-11 assigned accession CGMCC No. 21745;
   the *Lactobacillus fermentum* is *Lactobacillus fermentum* AI-25 assigned accession CGMCC No. 21746;
   the *Lactobacillus plantarum* is *Lactobacillus plantarum* AI-66 assigned accession CGMCC No. 21741;
   the *Lactobacillus casei* is *Lactobacillus casei* AI-12 assigned accession CGMCC No. 21742;
   the *Lactobacillus acidophilus* is *Lactobacillus acidophilus* AI-32 assigned accession CGMCC No. 21743;
   the *Lactobacillus paracasei* is *Lactobacillus paracasei* AI-62 assigned accession CGMCC No. 21744;
   the *Lactobacillus reuteri* is *Lactobacillus reuteri* AI-70 assigned accession CGMCC No. 21748;
   the *Bifidobacterium animalis* subsp. *lactis* is *Bifidobacterium animalis* subsp. *lactis* AI-01 assigned accession CGMCC No. 21747;
   the *Bifidobacterium infantis* is *Bifidobacterium infantis* AI-20 assigned accession CGMCC No. 21779; and
   the *Bifidobacterium bifidum* is *Bifidobacterium bifidum* AI-91 assigned accession CGMCC No. 21780.

2. The method of claim 1, wherein the probiotic is a combination of the *Lactobacillus rhamnosus* and the *Lactobacillus fermentum*, a combination of the *Lactobacillus casei* and the *Bifidobacterium animalis* subsp. *Lactis*, or a combination of the *Lactobacillus paracasei* and the *Bifidobacterium infantis*.

3. A method for treating atherosclerosis in a subject in need thereof, comprising:
   inoculating a probiotic into a fermentation medium followed by anaerobic culture to obtain a fermentation broth; and
   administering a therapeutically effective amount of the fermentation broth to the subject;
   wherein the probiotic comprises a microorganism selected from the group consisting of *Lactobacillus rhamnosus, Lactobacillus fermentum, Lactobacillus plantarum, Lactobacillus casei, Lactobacillus acidophilus, Lactobacillus paracasei, Lactobacillus reuteri, Bifidobacterium animalis* subsp. *lactis, Bifidobacterium infantis, Bifidobacterium bifidum* and a combination thereof; and
   the *Lactobacillus rhamnosus* is *Lactobacillus rhamnosus* AI-11 assigned accession CGMCC No. 21745;
   the *Lactobacillus fermentum* is *Lactobacillus fermentum* AI-25 assigned accession CGMCC No. 21746;
   the *Lactobacillus plantarum* is *Lactobacillus plantarum* AI-66 assigned accession CGMCC No. 21741;
   the *Lactobacillus casei* is *Lactobacillus casei* AI-12 assigned accession CGMCC No. 21742;
   the *Lactobacillus acidophilus* is *Lactobacillus acidophilus* AI-32 assigned accession CGMCC No. 21743;
   the *Lactobacillus paracasei* is *Lactobacillus paracasei* AI-62 assigned accession CGMCC No. 21744;
   the *Lactobacillus reuteri* is *Lactobacillus reuteri* AI-70 assigned accession CGMCC No. 21748;
   the *Bifidobacterium animalis* subsp. *lactis* is *Bifidobacterium animalis* subsp. *lactis* AI-01 assigned accession CGMCC No. 21747;
   the *Bifidobacterium infantis* is *Bifidobacterium infantis* AI-20 assigned accession CGMCC No. 21779; and
   the *Bifidobacterium bifidum* is *Bifidobacterium bifidum* AI-91 assigned accession CGMCC No. 21780.

4. The method of claim 3, wherein the probiotic is a combination of the *Lactobacillus rhamnosus* and the *Lac-*

*tobacillus fermentum*, a combination of the *Lactobacillus casei* and the *Bifidobacterium animalis* subsp. *Lactis*, or a combination of the *Lactobacillus paracasei* and the *Bifidobacterium infantis*.

* * * * *